(12) United States Patent
Eberth et al.

(10) Patent No.: US 10,611,991 B2
(45) Date of Patent: Apr. 7, 2020

(54) PULSATILE PERFUSION BIOREACTOR FOR MIMICKING, CONTROLLING, AND OPTIMIZING BLOOD VESSEL MECHANICS

(71) Applicant: University of South Carolina, Columbia, SC (US)

(72) Inventors: John F. Eberth, Columbia, SC (US); Tarek Shazly, Columbia, SC (US); Boran Zhou, Columbia, SC (US); David A. Prim, Columbia, SC (US); Conrad Michael Gore, West Columbia, SC (US)

(73) Assignee: University of South Carolina, Columbia, SC (US)

( * ) Notice: Subject to any disclaimer, the term of this patent is extended or adjusted under 35 U.S.C. 154(b) by 290 days.

(21) Appl. No.: 15/071,354

(22) Filed: Mar. 16, 2016

(65) Prior Publication Data

US 2016/0298073 A1    Oct. 13, 2016

Related U.S. Application Data

(60) Provisional application No. 62/143,844, filed on Apr. 7, 2015.

(51) Int. Cl.
*C12M 1/00* (2006.01)
*C12M 1/34* (2006.01)
(Continued)

(52) U.S. Cl.
CPC ............ *C12M 29/12* (2013.01); *C12M 21/08* (2013.01); *C12M 25/10* (2013.01); *C12M 29/00* (2013.01);
(Continued)

(58) Field of Classification Search
CPC ....................................................... C12M 29/12
(Continued)

(56) References Cited

U.S. PATENT DOCUMENTS

2004/0058432 A1* 3/2004 Owen ...................... A01N 1/02
435/284.1
2009/0269841 A1* 10/2009 Wojciechowski ..... C12M 23/28
435/325

(Continued)

OTHER PUBLICATIONS

Huang et al., "Engineering of arteries in vitro", Cellular and Molecular Life Sciences, 71, 2014, pp. 2103-2118.
(Continued)

*Primary Examiner* — Kevin Joyner
*Assistant Examiner* — Holly M Mull
(74) *Attorney, Agent, or Firm* — Dority & Manning, P.A.

(57) ABSTRACT

A pulsatile perfusion bioreactor for culturing one or more engineered blood vessels having a lumen and a wall is provided. The bioreactor includes a chamber for holding the engineered blood vessel and cell culture media; a mechanical property monitoring system for measuring axial tensile stress and strain, circumferential tensile stress and strain, and/or shear stress imparted on the vessel wall; and a pump system for delivering cell culture media through the vessel lumen, wherein the vessel is exposed to a composite pressure waveform and a composite flow waveform as the media is delivered there through. The pump system includes a steady flow and peristaltic pumps. Further, the composite pressure and flow waveforms each include a mean component, a fundamental frequency component, and a second harmonic frequency component. The bioreactor also includes a computer interface for monitoring and adjusting the composite waveforms to maintain a predetermined stress levels.

13 Claims, 8 Drawing Sheets

(51) Int. Cl.
*C12M 3/00* (2006.01)
*A61F 2/06* (2013.01)
*C12N 5/071* (2010.01)
*C12M 1/42* (2006.01)
*C12M 1/12* (2006.01)
*A61L 27/00* (2006.01)

(52) U.S. Cl.
CPC .......... *C12M 29/10* (2013.01); *C12M 35/04* (2013.01); *C12M 41/40* (2013.01); *C12N 5/0691* (2013.01)

(58) Field of Classification Search
USPC ...................................................... 435/289.1
See application file for complete search history.

(56) References Cited

U.S. PATENT DOCUMENTS

2014/0127795 A1* 5/2014 Dancu ................... G01N 21/47
 435/289.1
2016/0331511 A1* 11/2016 Kassab .................. A61L 27/26

OTHER PUBLICATIONS

Jay D. Humphrey, "Mechanisms of Arterial Remodeling in Hypertension, Couples Roles of Wall Shear and Intramural Stress", Hypertension, 52, 2008, pp. 195-200.
Konig et al., "A Pulsatile Bioreactor for Conditioning of Tissue-Engineered Cardiovascular Constructs under Endoscopic Visualization" Journal of Functional Biomaterials, 3, 2012, pp. 480-496.
Noam Saul Lightstone, "Design of Bioreactor to Mimic Hemodynamic Shear Stresses on Endothelial Cells in Microfluidic Systems", Thesis, 2014, 386 pages.
McFetridge et al., "Design of Vascular Graft Bioreactors", Bioreactors for Tissue Engineering, 2005, pp. 269-283.
Pittman et al., "Arterial and Central Venous Pressure Monitoring", Lippincott Williams & Wilkins, 18 pages.
Zaucha et al., "A Novel Cylindrical Biaxial Computer-Controlled Bioreactor and Biomechanical Testing Device for Vascular Tissue Engineering", Tissue Engineering: Part A, vol. 15, No. 11, 2009, 10 pages.

* cited by examiner

PULSATILE PERFUSION BIOREACTOR FOR MIMICKING, CONTROLLING, AND OPTIMIZING BLOOD VESSEL MECHANICS

RELATED APPLICATIONS

The present application claims priority to U.S. Provisional Application Ser. No. 62/143,844, filed on Apr. 7, 2015, which is incorporated herein in its entirety by reference thereto.

BACKGROUND

The field of vascular tissue engineering seeks to generate functional blood vessels with properties similar to that of healthy tissue. Engineered tissues may originate from biocompatible scaffolds embedded with diverse populations of cells or through altering existing tissues exposed to controlled stimulation that initiate known intrinsic adaptive processes. The demand for such functional tissues is especially great in the vascular system, where engineered blood vessels (EBVs) could be used to replace diseased or damaged blood vessels in patients suffering from advanced stage atherosclerosis or other focalized degenerative diseases. For example, nearly 400,000 coronary artery bypass grafts and around 50,000 peripheral vascular grafts were performed in the United States each year. However, patients often lack viable autograft tissue and purely synthetic replacements (e.g., DACRON® grafts) become occluded when used to replace small diameter vessels. As such, there is a need for the development of functional EBVs that are biocompatible, are anti-thrombogenic, and that exhibit autograft-like levels of burst and fatigue strength. Accordingly, various approaches have been employed over the years to engineer blood vessels that meet these requirements, yet few have reached advanced stage clinical trials. Therefore the practical and commercial development of this technology remains an emerging field.

In the development of EBVs, the choice of scaffold material, cell type, and assembly are typically considered. The mechanical environment and the bioreactor utilized for culturing the EBV must also be considered. The mechanical environment includes the biaxial stresses and stretches generated in the circumferential and the axial directions of the EBV, as well as the fluid-induced wall shear stresses focused along the endothelial cell (EC) lined lumen of the EBV. In vivo, the circumferential loading is a result of pressurization and the axial loading is a result of somatic growth. It has also been observed that natural tissues seek to restore levels of mechanical stress. For example, in sustained hypertension, which elicits an acute increase in circumferential wall stress, the primary remodeling outcome is an increase in wall thickness, which in turn acts to restore the wall stress to baseline, or normotensive, stress levels. Accordingly, the mechanical environment has been identified as a major contributor to the growth and remodeling of a biomimetic EBV and is an important physical factor in vascular graft generation and homeostasis. Specifically, cyclic stretching of intramural vascular cells initiates proliferation, promotes the release of growth factors, alters fiber realignment, regulates smooth muscle cell (SMC) contractile phenotype, and encourages overall extracellular matrix (ECM) synthesis (e.g., collagen, tropoelastin, etc.) and tissue turnover by SMCs and fibroblasts. Similarly, the frequency, direction, and magnitude of shear stress on ECs governs metabolic activities, nutrient exchange, cellular morphology, stress fiber alignment, and SMC phenotype, and also control paracrine factors including nitric oxide release, which is a major mediator of remodeling and homeostasis.

Over the last fifty years, vascular perfusion bioreactors have been developed primarily as research tools but have recently become available in the commercial market. However, commercially available bioreactors are not designed to implement the comprehensive mechanical objectives discussed above that are needed to create a truly biomimetic EBV. As such, a need exists for a EBV bioreactor that has the capability to optimize mechanical (stress) objectives, which would, in turn, minimize culture time and maximize output. Furthermore, a need exists for a bioreactor specific for culturing EBVs that can impose and test biaxial loads, can deliver specific biomimetic pressure and flow profiles, can be scalable for different vessels and animals, and can provide for real time data collection and assessment. A need also exists for a bioreactor that can be autoclaved, maintain sterility for prolonged culture times, promote nutrient and gas exchange, actively maintain temperature and pH, permit cell seeding, and allow for chemical stimulation and assessment. Such a device could be used in the commercial setting and not solely as a research tool.

Moreover, the ultimate success of an EBV lies in its ability to perform in the intended environment. The biomimetic hemodynamic loads on the EBV are unique amongst species and anatomical location, thus the knowledge and application of vessel-specific hemodynamics and axial loading that mimic the intended graft condition are both crucial during tissue development in order to avoid hemodynamically-induced pathologies. As such, a need exists for a bioreactor that could prescribe dynamic pressure and flow waveforms during culture that incorporate complex phasic relationships that are not static or simply sinusoidal. In other words, a need exists for a bioreactor that can deliver variable stresses to an engineered blood vessel through the application and control of dynamic pressure and flow waveforms so that the engineered blood vessel can be conditioned and remodeled during ex-vivo culture so that it ultimately possesses properties that mimic a native blood vessel.

SUMMARY OF THE INVENTION

The present invention is directed to a pulsatile perfusion bioreactor for culturing one or more engineered blood vessels having a lumen and a wall. This invention also provides mechanomimetic stimulation to the blood vessels and can be used to study physiological dependent vascular processes such as the response to endovascular interventions and pharmaceutical administration. The pulsatile perfusion bioreactor includes one or more chambers for holding the engineered blood vessel and cell culture media; a mechanical property monitoring system for measuring axial tensile stress, circumferential tensile stress, shear stress, or a combination thereof imparted on the wall of the engineered blood vessel and for measuring and controlling axial stretch, circumferential stretch, or a combination thereof imparted on the wall of the engineered blood vessel; and a pump system for delivering cell culture media through the lumen of the engineered blood vessel. The pump system includes a steady flow pump and a peristaltic pump such that when cultured inside the pulsatile perfusion bioreactor, the engineered blood vessels are exposed to a composite pressure waveform and a composite flow waveform as the cell culture media is delivered through the lumen. The composite pressure waveform comprises a mean pressure component, a fundamental frequency (or first harmonic) pressure component and a second harmonic frequency pressure component, while the composite flow waveform component comprises a mean flow component, a fundamental frequency (or first harmonic) flow component and a second harmonic frequency flow component. However, it is to be understood that additional harmonic flow frequencies can be added to improve resolution. The pulsatile perfusion bioreactor further includes a computer interface for monitoring and adjusting the composite pressure waveform, the composite flow waveform, or a combination thereof to maintain a predetermined axial tensile stress level, a predetermined circumferential stress level, a predetermined shear stress level, or a combination thereof.

In an additional embodiment, the composite pressure waveform and the composite flow waveform can be derived from a pressure waveform and a flow waveform of a native blood vessel, and the engineered blood vessel can be a replacement for the native blood vessel.

In another embodiment, the steady flow pump can deliver the mean pressure component of the composite pressure waveform and the mean flow component of the composite flow waveform. In still another embodiment, the peristaltic pump can deliver a pulsatile flow of cell culture media through the lumen via a first pump head and a second pump head. For example, the first pump head can provide the fundamental frequency pressure component of the composite pressure waveform and the fundamental frequency flow component of the composite flow waveform, while the second pump head can provide the second harmonic frequency pressure component of the composite pressure waveform and the second harmonic frequency flow component of the composite flow waveform. In a further embodiment, the peristaltic pump can also include a third pump head, where the third pump head can provide a third harmonic frequency pressure component of the composite pressure waveform and a third harmonic frequency flow component of the composite flow waveform.

In yet another embodiment, the bioreactor can also include a compliance chamber. In one more embodiment, the bioreactor can include a pressure transducer. In an additional embodiment, the bioreactor can also include a stepper motor controlled pinch valve. In one particular embodiment, the bioreactor can also include a camera for measuring the engineered blood vessel length, wall diameter, wall thickness, or a combination thereof.

In one embodiment, the bioreactor chamber can be located in an incubator. Further, the engineered blood vessel can include a natural material or a synthetic material. Moreover, the engineered blood vessel can include endothelial cells, smooth muscle cells, or a combination thereof.

In yet another embodiment, the present invention is directed to a method of culturing one or more engineered blood vessels having a lumen and a wall inside a pulsatile perfusion bioreactor. The method includes inserting the engineered blood vessel to be cultured into a chamber; filling the chamber with cell culture media; delivering cell culture media through the lumen of the engineered blood vessel via a pump system, wherein the engineered blood vessel is exposed to a composite pressure waveform and a composite flow waveform as the cell culture media is delivered through the lumen, the pump system comprising a steady flow pump and a peristaltic pump, wherein the composite pressure waveform comprises a mean pressure component, a fundamental frequency pressure component and a second harmonic frequency pressure component, and wherein the composite flow waveform component comprises a mean flow component, a fundamental frequency flow component, and a second harmonic frequency flow component; measuring axial tensile stress, circumferential tensile stress, shear stress, axial stretch, circumferential stretch, or a combination thereof imparted on the wall of the engineered blood vessel via a mechanical property monitoring system; and monitoring and adjusting the composite pressure waveform, the composite flow waveform, or a combination thereof to maintain a predetermined axial tensile stress level, a predetermined circumferential stress level, a predetermined shear stress level, a predetermined axial stretch level, a predetermined circumferential stretch level, or a combination thereof via a computer interface.

In an additional embodiment, the composite pressure waveform and the composite flow waveform can be derived from a pressure waveform and a flow waveform of a native blood vessel, and the engineered blood vessel can be a replacement for the native blood vessel.

In another embodiment, the steady flow pump can deliver the mean pressure component of the composite pressure waveform and the mean flow component of the composite flow waveform.

In still another embodiment, the peristaltic pump can deliver a pulsatile flow of cell culture media through the lumen. The peristaltic pump can include a first pump head and a second pump head, where the first pump head can provide the fundamental frequency pressure component of the composite pressure waveform and the fundamental frequency flow component of the composite flow waveform, while the second pump head can provide the second harmonic frequency pressure component of the composite pressure waveform and the second harmonic frequency flow component of the composite flow waveform.

In yet another embodiment, the peristaltic pump can further include a third pump head, where the third pump head provides a third harmonic frequency pressure component of the composite pressure waveform and a third harmonic frequency flow component of the composite flow waveform.

In an additional embodiment, the pulsatile perfusion bioreactor can include a compliance chamber, where the compliance chamber can facilitate adjustment of the composite pressure waveform and can reduce noise caused by the peristaltic pump. In still another embodiment, pressure can be measured via a pressure transducer and a stepper motor controlled pinch valve can be utilized to adjust resistance within the pulsatile perfusion bioreactor, wherein adjusting the resistance results in an adjustment to the pressure.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

Figure 1:
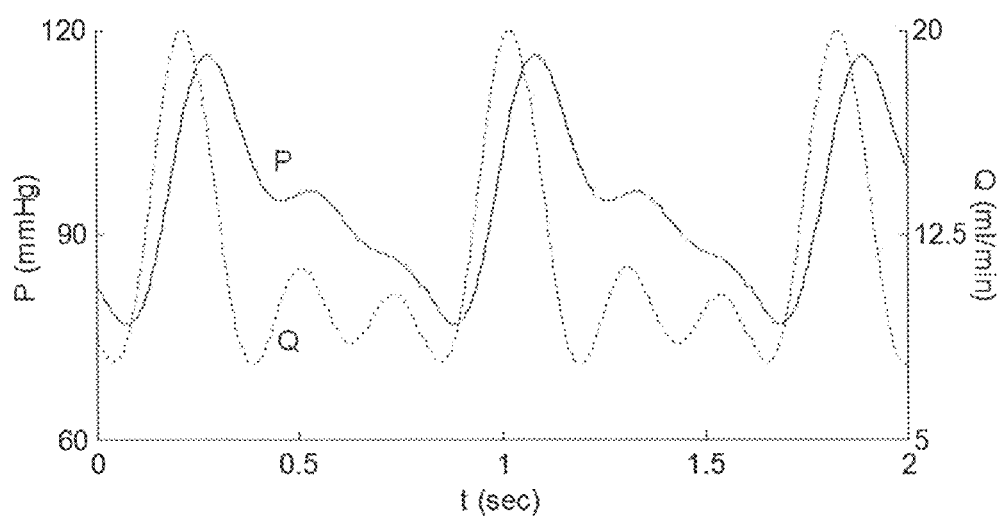
FIG. 1 shows an example of the physiological blood pressure (P) and flow (Q) waveforms that can be created an applied to an EBV via the pulsatile perfusion bioreactor of the present invention. This example mimics the conditions of a human radial artery.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

It is understood that mechanical signals are key mediators of the cellular processes which underlie blood vessel remodeling, including proliferation, differentiation, migration, and protein synthesis. Further, blood vessels are dynamic in form, function, and pulsatility (i.e., the difference between the maximum and minimum blood pressure and flow). Blood pressure induces periodic circumferential stresses, which are sensed by smooth muscle cells and fibroblasts embedded in the vascular wall, whereas blood flow induces periodic and often oscillatory wall shear stresses, which are sensed by endothelial cells lining the lumen. In addition, it has been shown that the production of extracellular matrix material and the alignment of smooth muscle cells and fibroblasts both depend on the rate and magnitude of cyclic stretching. Furthermore, gene profiles of endothelial cells in culture are dependent upon the magnitude and frequency of flow oscillation with a morphology that discriminates between different flow environments. Vascular pathologies also depend on the cyclic and oscillatory flow such as those observed in atherosclerosis formation. Thus, blood vessel growth and remodeling are highly dependent on the pressure and flow waveforms and stresses to which the blood vessel is exposed. As such, an accurate means of applying pressure and flow waveforms to a EBV and adjusting the pressure and flow waveforms to achieve desired stress and loading objectives is important in obtaining a truly biomimetic EBV and can be accomplished via the pulsatile perfusion bioreactor of the present invention.

Meanwhile, although in-vivo and ex-vivo experimental studies have been conducted to delineate remodeling outcomes under prescribed loading conditions, with a manifest dependence on vascular wall stresses, no ex-vivo culture systems are available that can accurately translate remodeling principles (i.e., stress-driven growth) into the development of commercially available EBVs, where the amount of stress applied to the EBV can be accurately controlled during culturing so that the engineered blood vessel is exposed to stresses equivalent to those to which a native blood vessel is exposed. This is due, in part, to the complexity of conferring biomimetic pulsatile loading in a three-dimensional tissue culture environment that integrates both the fluid and solid domains, the challenges of retaining tissue viability for extended culture periods, and the wide variation in the types and sizes of EBVs to be cultured. Furthermore, stress levels imparted to an EBV must be tightly controlled throughout culture, as exceeding material and maturation state-specific stress thresholds can lead to material failure or potentially adverse cellular responses (i.e., apoptosis). To solve this problem, the pulsatile perfusion bioreactor of the present invention can accurately replicate the pressure and flow waveforms of the native vessel that the EBV is intended to replace and can make real time adjustments to the waveforms as the EBV is cultured to maintain desired stress levels. As such, the present inventors have found that an EBV cultured in the pulsatile perfusion bioreactor of the present invention can undergo remodeled during culture so that the end product mimics the native vessel it is to replace.

As discussed in more detail below, the present inventors have developed an ex-vivo pulsatile perfusion bioreactor that enables for the control of mechanically-induced tissue growth and remodeling of an EBV that closely mimics in vivo conditions via the application of specified stress levels through the control of pressure and flow waveforms applied to the EBV in culture. In other words, the pulsatile perfusion bioreactor of the present invention can control deterministic aspects of blood vessel mechanics and can facilitate functional vascular tissue remodeling in engineered blood vessels having a synthetic or biological origin. For instance, through application of biomimetic pressure and flow waveforms and real-time assessment of sample geometry and mechanical properties, the pulsatile perfusion bioreactor of the present invention enables the control and optimization of culture conditions for various sizes and types of engineered vascular tissues formed from both natural and synthetic materials. Further, the pulsatile perfusion bioreactor of the present invention allows for collection of sample data using a computer interface with minimal human intervention, thus mitigating contamination potential and enabling a feedback control system for optimizing vascular tissue growth. Dynamic flow-induced wall shear stress and three-dimensional tensile wall stress conditions can be controlled and adjusted to predetermined objective values based on the type of native blood vessel being replaced with the EBV, and flow/pressure profiles and imposed axial stretch can be tuned and adjusted during culture to maintain the predetermined objective values, resulting in a EBV having properties that mimic those of the native blood vessel that it will replace. Furthermore, the mechanical suitability of EBV can be tested directly within the pulsatile perfusion bioreactor of the present invention, which can streamline the iterative refinement of culture protocol that is implicit in the development of any tissue-engineered product.

In addition, while currently available bioreactors enable specification of the global mechanical environment of vascular tissue samples (e.g., lumen pressure, flow rate, and axial extension), the pulsatile perfusion bioreactor of the present invention additionally allows for specification of the local mechanical environment of resident vascular cells (e.g., wall tensile stresses (circumferential and axial) and flow-induced shear stress). This is a critical distinction, as the local mechanical environment changes as the vessel remodels and is what drives mechanosensitive cellular processes. The pulsatile perfusion bioreactor of the present invention can thus consistently impart biomimetic stresses to the EBV being cultured, and that tissue viability and function can be retained at least over a two-week culture period. Irrespective of the particular application, the pulsatile perfusion bioreactor of the present invention is configured to allow for the automated control of fundamental mechanical signals governing vascular tissue remodeling. The driving mechanical stimuli for native vascular tissue growth and remodeling are wall stresses operative at the intima (e.g., flow-induced shear stress, which is sensed and regulated by vascular endothelial cells) and within the media (e.g., tensile stress in the axial and circumferential directions, which is sensed and regulated by vascular smooth muscle cells) of a blood vessel. Thus, the ability to control these same mechanical quantities in a bioreactor can elicit control of growth and remodeling processes in cell-laden EBVs. In order to promote the cellular processes implicit in vascular tissue generation, it is critical that imposed stresses are derived from biomimetic mechanical loading profiles (i.e., physiological pressure and flow waveforms). The application of biomimetic mechanical loading on the EBV culture in the pulsatile perfusion bioreactor of the present invention via the application of pressure and flow waveforms that mimic physiological pressure and flow waveforms can thus create an ex-vivo environment in which vascular cell behavior can be understood, predicted, and ultimately directed towards functional engineered tissue generation.

As mentioned above, currently available bioreactor systems feature control of the lumen pressure, flow rate, and in some cases the degree of axial stretch to which samples are subjected, (i.e., control of the global mechanical loading). Further, such bioreactors utilize pressure and flow waveforms that are gross approximations of physiologic loading (e.g., sine waves or steady flows) such that the resulting mechanical environment in which an EBV is cultured substantially deviates from that of native vessels. In contrast, the pulsatile perfusion bioreactor of the present invention allows for user control of the wall stress imparted on the EBV, and thus imparts the user with the ability to control of the local mechanical environment which drives key cellular processes. Such control is due to the use and application of pressure and flow waveforms that replicate native hemodynamics.

In order to control the local mechanical environment via the pulsatile perfusion bioreactor of the present invention, predetermined wall stress values can be programmed and automatically maintained through a feedback loop that integrates mechanical and geometrical information obtained through measurements performed on the EBV by a mechanical property monitoring system that is a component of the pulsatile perfusion bioreactor. Thus, as the EBV changes dimensions and/or mechanical properties as a consequence of the progression of the growth and remodeling processes, the loading imposed on the EBV by the pulsatile perfusion bioreactor system can be automatically tuned such that predetermined stress values are maintained. Thus, the pulsatile perfusion bioreactor of the present invention is configured to control and optimize the stimuli-response mechanisms which underpin vascular tissue growth. The various components of the pulsatile bioreactor of the present invention are discussed in more detail below.

Applied Pressure and Flow Waveforms

Before the pulsatile perfusion bioreactor system of the present invention can be programmed and used for the culture of an engineered blood vessel, the pressure and flow waveforms to be applied during culture to achieve the desired stress or loading levels must be determined. It is known that the shape, peak, minimum, and average values of blood pressure and flow vary greatly amongst various vascular tissues. Similarly, hemodynamic and geometric differences exist between different mammalian species, even when comparing similar anatomical locations (e.g., the ascending aorta). These waveforms are modified by the different downstream reflections, the relative size of blood to blood vessel, and most notably the diversity in heart rate. Accordingly, pressure and flow waveforms often do not have the same shape and cannot be accurately modeled as simple sine waves. Thus, these hemodynamic waveforms have been quantified using the mean, fundamental (first harmonic), and additional harmonic components of a Fourier series representation. Further, the electro-hydraulic analogy provides a convenient methodology enabling a translation of periodic hemodynamic qualities into electrical circuits where Fourier analysis is commonplace. Here the voltage, current, capacitance, resistance, and inductance are represented as pressure, flow rate, compliance, resistance and inertia. The simplicity of this technique makes it well suited for the practicality of the laboratory bench as physical structures are represented by pumps, valves, compliance chambers, and culture media.

As shown in FIG. 1, the typical pressure (P) and flow (Q) waveforms for a blood vessel are complex and are not simple sine waves or steady flows. After the pressure and flow waveforms similar to those shown in FIG. 1 are determined for the specific native vessel to be replicated as a EBV in order to achieve desired stress levels to promote the culture of the EBV in a biomimetic environment, the waveforms are converted into mathematical expressions that can be applied to the EBV positioned inside the pulsatile perfusion bioreactor of the present invention via a computer interface and specific hardware (e.g., a compliance chamber, pinch valve, etc.).

Specifically, the present inventors have taken the pressure and flow profiles for various types of blood vessels in their native environment and have then converted those waveforms to mathematical models via Fourier Transform, where the mathematical models are then used to recreate the pulsatile flow and pressure waveforms experienced by a native vessel during the culture of a EBV in the pulsatile perfusion bioreactor of the present invention. Such a determination can be based on Womersley's approach, which uses a periodic pressure gradient to predict the temporal velocity profile within a vessel. This profile does not follow a constant parabolic shape throughout the cardiac cycle, can exhibit flow reversal, and may have a maximum velocity that is not necessarily at the center of the lumen of the vessel. However, centerline velocity can be easily measured and can be performed non-invasively with modern approaches such as vascular Doppler, so the present inventors have utilized this approach. Further, to calculate other hemodynamic variables of interest, namely volumetric flow rates, velocity profiles, and wall shear stresses from the measured centerline velocity, the present inventors have utilized an inverse Womersley approach to provide both temporal and spatial blood flow quantities for various types of blood vessels for which replacement EBVs can be cultured utilizing the pulsatile perfusion bioreactor of the present invention.

As a result of the transformation of the pressure and flow waveforms into mathematical expressions, multiple waveforms can be applied to the EBV, resulting in a composite pressure waveform and a composite flow waveform. Each composite waveform can include a mean pressure component, a fundamental frequency component (e.g., a first harmonic frequency component), and additional harmonic frequency components. While in the past, literature has indicated that a fundamental frequency component plus four additional harmonic frequency components are required was required to accurately replicated the pressure and flow waveforms to which a native blood vessel is exposed, the present inventors have surprisingly found that an accurate model of composite pressure and flow waveforms and be developed utilizing less than four additional harmonic frequency components. For instance, in one particular embodiment, the composite pressure and flow waveforms includes a mean or steady component, a first harmonic frequency component (also referred to as the fundamental frequency component), and a second harmonic frequency component. In a further embodiment, the composite pressure and flow waveforms can include a third harmonic frequency component. Moreover, although not required, additional harmonic frequency components can be employed in the composite pressure and flow waveforms to achieve composite waveforms that most closely mimic the waveforms to which the native blood vessel of interest is exposed, resulting in the EBV being exposed to biomimetic tensile and shear stresses. In other words, it is to be understood that any suitable number of harmonic frequencies can be utilized up to an $n^{th}$ harmonic frequency, where n is a whole number that is 2 or greater.

One process for deriving the composite pressure and flow waveforms that can be programmed into a computer interface is described in more detail below in Example 1.

Bioreactor Components

Figure 2:
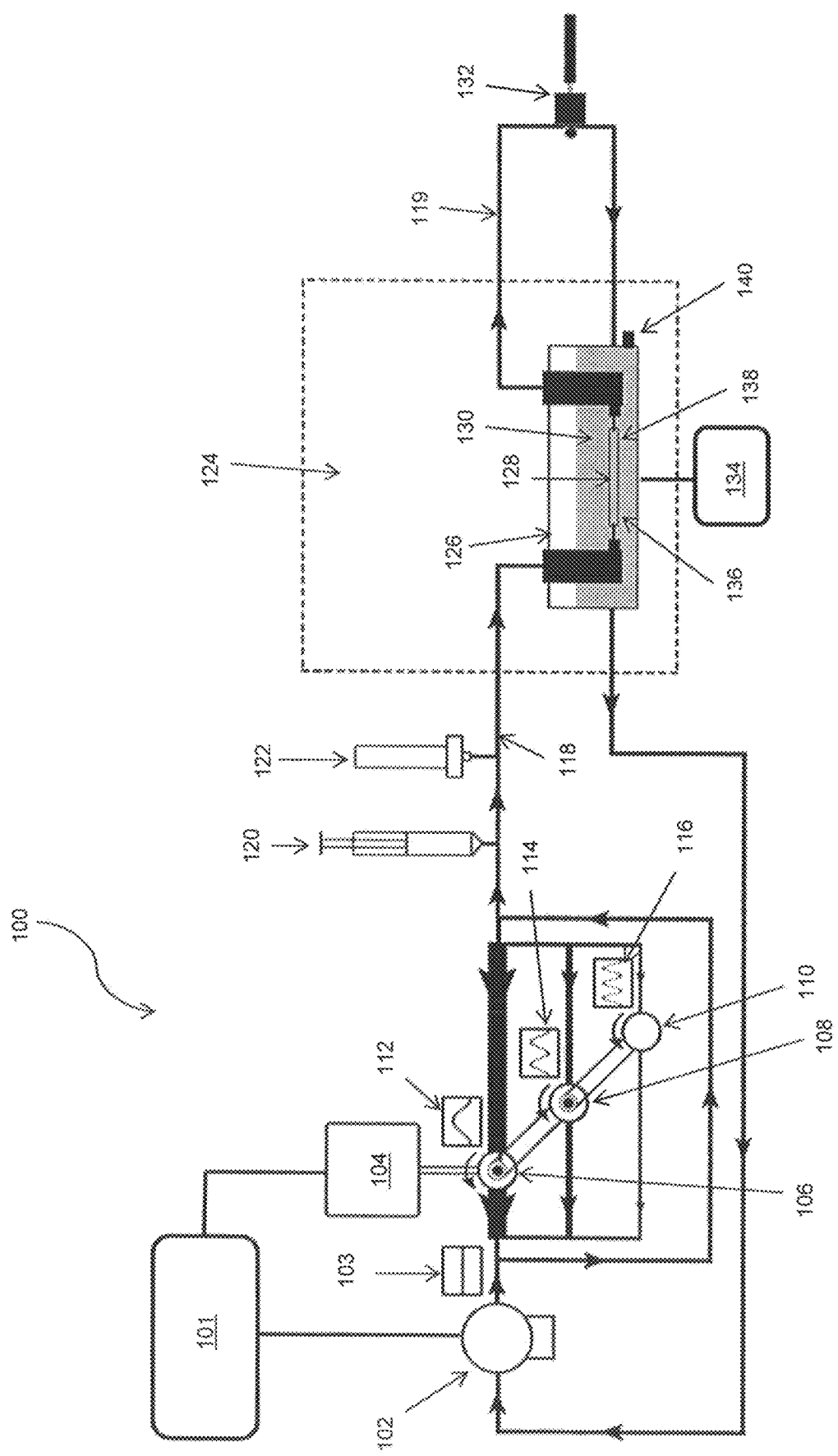
FIG. 2 shows a schematic of one embodiment of the pulsatile perfusion bioreactor of the present invention.

Once the waveforms to be applied to the EBV are determined, the process for culturing the EBV in the pulsatile perfusion bioreactor of the present invention can be initiated. Referring to FIG. 2, in one embodiment of the present invention, the pulsatile perfusion bioreactor 100 includes a computer interface 101 that controls a pump system that can include a steady flow pump 102 that can deliver a mean flow and pressure waveform 103 and a peristaltic pump 104, which can include multiple pump heads depending on the number of harmonic frequency components to deliver as part of the composite pressure and flow waveforms. For instance, as shown in FIG. 2, the peristaltic pump can include a first pump head 106, a second pump head 108, and a third pump head 110 to deliver a first harmonic frequency component 112 (i.e., the fundamental frequency component), a second harmonic frequency component 114, and, optionally, a third harmonic frequency component 116. Additional harmonic frequency components of the composite waveforms can be incorporated into the pump system via additional pump heads.

In one particular embodiment of the pulsatile perfusion bioreactor 100 of the present invention, the computer interface 101 is programmed such that cell culture media is introduced via the pump system into the lumen of an engineered blood vessel (EBV) 128 being cultured in a bioreactor chamber 126 positioned inside an incubator 124, such that the EBV 128 is subjected to the composite pressure waveform and the composite flow waveform from the programmed mean flow 103 and harmonic frequency waveforms 112, 114, and 116. The EBV 128 is positioned in the bioreactor chamber 126, which is filled with cell culture media 130, where the media can be introduced and replaced via media exchange port 140. In addition, media is delivered through the proximal end 136 of the EBV 128 in a pulsatile manner via inlet tubing 118 in the form of the composite flow waveform discussed above and can then be circulated through the lumen of the EBV 128 and returned to the pump system via outlet tubing 119. The composite waveforms discussed above can be applied to the EBV 128 and monitored and adjusted, along with axial wall stretch, via a feedback loop as growth and remodeling of the EBV 128 progresses to maintain the desired level of tensile and shear wall stresses on the EBV. For instance, utilizing measurements recorded via a mechanical property monitoring system 134, which can include tensile testing components, a camera, etc. (not shown), a stepper motor controlled pinch valve 132 located at a distal end 140 of the EBV 128 can be adjusted to control the pressure applied to the EBV 128 as tracked via a pressure transducer 120 integrated into the pulsatile perfusion bioreactor 100, while a compliance chamber 120 can also be used to make adjustments to the pulsatility of the applied waveforms. The mechanical property monitoring system 134 can also include a force transducer to measure static and dynamic axial forces. From these forces, a real-time assessment of the static and dynamic stresses can be calculated. Further, a pair of electronic linear stages (not shown) can be used to apply static or dynamic axial stretching to the EBV as desired.

Figure 3A:
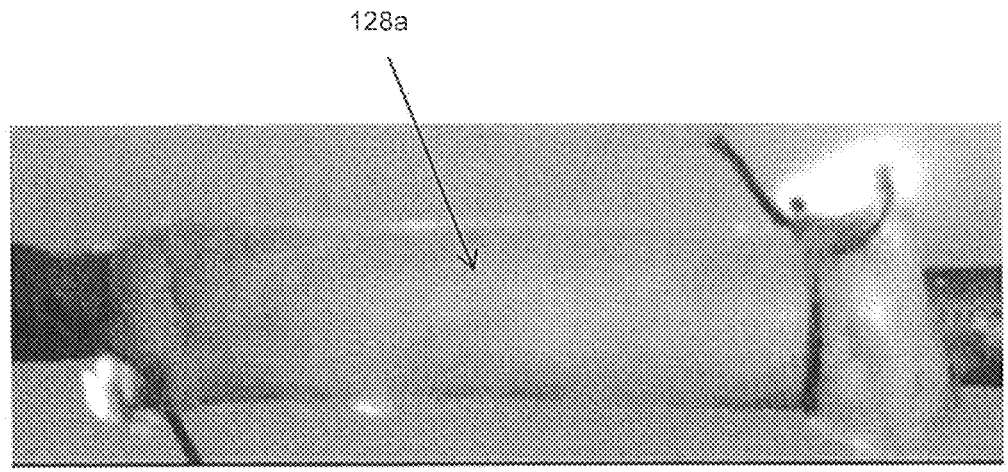
FIG. 3a shows a porcine renal artery cultured for 10 days in the pulsatile perfusion bioreactor of the present invention prior to administration of phenylephrine to elicit smooth muscle cell (SMC) contraction.
Figure 3B:
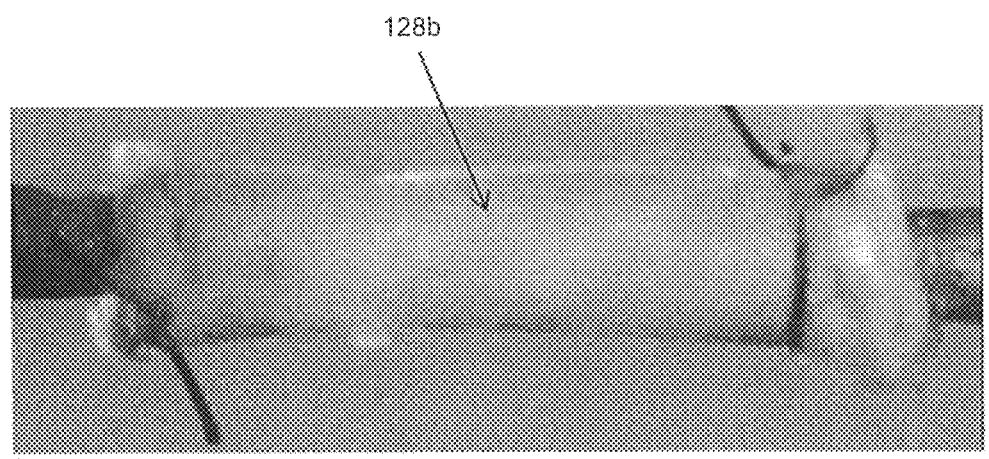
FIG. 3b shows a porcine renal artery cultured for 10 days in the pulsatile perfusion bioreactor of the present invention after administration of phenylephrine to elicit smooth muscle cell (SMC) contraction.

The aforementioned pulsatile perfusion bioreactor 100 can successfully culture a EBV 128 over an extend period of time, such as up to about 10 days, as shown via a comparison of FIGS. 3a and 3b. For instance, FIG. 3a shows a porcine renal artery 128a cultured for 10 days in the pulsatile perfusion bioreactor of the present invention prior to administration of phenylephrine to elicit smooth muscle cell (SMC) contraction. FIG. 3b shows a porcine renal artery 128b cultured for 10 days in the pulsatile perfusion bioreactor of the present invention after administration of phenylephrine to elicit smooth muscle cell (SMC) contraction. The ability of the porcine renal artery 128b to exhibit SMC contraction and EC dependent dilations demonstrates that the pulsatile perfusion bioreactor of the present invention can culture an EBV and demonstrate cell function afterwards. The present invention may be better understood with reference to the following example(s).

Example 1

Example 1 demonstrates the ability to determine the pressure and flow waveforms for various types of blood vessels in their native environment, which can then be converted to mathematical models via Fourier Transform, where the mathematical models can be used to recreate the pulsatile pressure and flow waveforms to which a native vessel is exposed during the culture of the EBVs of the present invention. Various waveform components can be combined to create composite pressure and flow waveforms to apply to the EBV via the pump system described above.
Introduction In Example 1, the groundwork for recreating native blood vessel hemodynamics for a EBV undergoing tissue culture in a pulsatile perfusion bioreactor is achieved by recreating the blood pressure and centerline flow velocity waveforms described in the classic and contemporary literature. These waveforms are digitized and represented as mathematical equations using a Fourier series reconstruction. The volumetric flow rates, found using an inverse Womersley approach, are used as the input into a 4-Element Windkessel electro-hydraulic analogy with best fit parameters that provide a basis for the design of the culture system components to match in vivo blood pressures. The time-dependent wall shear stresses and velocity profiles are calculated and compared from the literature sources providing groundwork for the identification of key hemodynamic features enabling intra- and inter-species comparisons.
Materials and Methods
Pulsatile Hemodynamics Arterial hemodynamics are characterized by cyclic pulsatility of both pressure and flow waveforms, the magnitude and behavior of which depend on cardiac contractility, the blood vessel location, and downstream resistances. In contrast, venous system hemodynamics consist predominantly of steady blood pressure and flow components. The in vivo, pulsatile, volumetric flow rate q(t) and wall shear stress $\tau_w(t)$ can easily be calculated when the temporal velocity profile u(r,t) is known using $$q(t) = 2\pi \int_0^{r_a} r u(r,t) dr \quad (1)$$

and $$\tau_w(t) = -\mu \frac{\partial u(r_a, t)}{\partial r}. \quad (2)$$

Here r is the radial location within the lumen of the vessel with fixed inner wall radii $r_a$ and $\mu$ is the viscosity of blood assumed to be constant at high shear rates.

From the momentum balance of Navier-Stokes, the governing equation for unsteady, axisymmetric laminar flow in a rigid tube, where gravitational effects are neglected is solved using the Womersley approach. The non-dimensional Womersley number to relates pulsatility to viscous effects at that frequency, so that $$\alpha_n = r_a (\omega_n \rho/\mu)^{1/2} \quad (3)$$

where $\rho$ is the density of blood and $\omega_n$ represents the heartbeat frequency with n=1 the fundamental frequency and n=2,3 the subsequent harmonics in rad/s.

Normally the entire velocity profile is unknown and only the centerline velocity u(0,t) profile is the only value reported (e.g., from pulsed wave Doppler). The complete velocity profile can be found from $$u(r,t) = u_s\left(1 - \frac{r^2}{r_a^2}\right) + \sum_{n=1}^{3} u_n(t)\left(\frac{J_0(i^{3/2}\alpha_n) - J_0(i^{3/2}\alpha_n r/r_a)}{J_0(i^{3/2}\alpha_n) - 1}\right) \quad (4)$$

where $u_s$ and $u_n(t)$ represent the steady and unsteady centerline velocities at each harmonic and where $J_0$ and $J_1$ are the Bessel functions of the first kind of zeroth and first order respectively. The volumetric flow rate can be found from the centerline velocity using equation (1) and (4)

$$q(t) = \pi r_a^2 \left( \frac{u_s}{2} + \sum_{n=1}^{3} u_n(t)\left(\frac{i^{3/2}\alpha_n J_0(i^{3/2}\alpha_n) - 2J_1(i^{3/2}\alpha_n)}{i^{3/2}\alpha_n J_0(i^{3/2}\alpha_n) - i^{3/2}\alpha_n}\right)\right) \quad (5)$$

Further, the time dependent wall shear stress at the wall can be found via $$\tau_w(t) = -\frac{\mu}{r_a}\left(-2u_s + \sum_{n=1}^{3} u_n(t)\left(\frac{i^{3/2}\alpha_n J_1(i^{3/2}\alpha_n)}{J_0(i^{3/2}\alpha_n) - 1}\right)\right). \quad (6)$$

Blood pressure (via catheterization) and flow waveforms are conveniently represented using a Fourier series expansion so that $$q(t) = \sum_{n=0}^{3} M_n^q \cos(\omega_n t + \phi_n^q) \quad (7)$$

and $$p(t) = \sum_{n=0}^{3} M_n^p \cos(\omega_n t + \phi_n^p), \quad (8)$$

where $M_n$ and $\phi_n$ are the magnitude and phase of pressure or flow waves at each frequency. Of note, blood pressure and flow have the same $\omega_n$ but are out of phase.

When volumetric flow is given in the form of equation (7) instead of the centerline velocity, the wall shear stress can also be calculated directly using the inverse Womersley approach, so that $$\tau_w(t) = \quad (9)$$

$$\frac{\mu}{\pi r_a^3}\left(4M_0^q - \sum_{n=1}^{3} M_n^q \cos(\omega_n t + \phi_n^q)\left(\frac{i^3 \alpha_n^2 J_1(i^{3/2}\alpha_n)}{i^{3/2}\alpha_n J_0(i^{3/2}\alpha_n) - 2J_1(i^{3/2}\alpha_n)}\right)\right)$$

and is sometimes the case in the literature. Equation (9) is convenient as it allows for a calculation of wall shear stress in a cultured vessel based on the magnitude of steady and pulsatile flow channels of the device described herein. These are described in the following section.
Electrical-Fluid Component Design The electro-hydraulic analogy employed by earlier researchers provides a basis for a lumped parameter estimation to recreate in-vivo hemodynamics. A pictorial representation of the electrical circuit with corresponding hydraulic elements is shown in FIG. 3. Application of Kirchhoff's current (volumetric flow) law yields two first order, linear, differential equations:

$$\frac{dp_1(t)}{dt} = \frac{q(t)}{C} - \frac{p_1(t)}{R_1 C} \quad (10)$$

and $$\frac{dp_2(t)}{dt} = R_2 \frac{dq(t)}{dt} - \frac{R_2 p_2(t)}{L} \quad (11)$$

where $p_1(t)$ and $p_2(t)$ are the pressures across resistors $R_1$ (mmHg·s/ml) and $R_2$ (mmHg·s/ml) respectively, C (ml/mmHg) is the downstream compliance, and L (mmHg·s²/ml) is the inductance. The volumetric flow rate represents the periodic displacement of a pump or pumps and is considered a configurable value in the pulsatile perfusion bioreactor of the present invention. Using Kirchoff's voltage (pressure) law, a third governing equation is obtained:

$$p(t) = p_1(t) + p_2(t) \quad (12)$$

with p(t) representing the pressure at the vessel culture location. A practical interpretation of these variables as they pertain to a physical design is provided in the results section.

Taking the Laplace transform of equations (10) to (12) provides a transfer function relating the volumetric flow input Q(s) to pressure output P(s) in the Laplace domain:

$$\frac{P(s)}{Q(s)} = \frac{R_1 R_2 C L s^2 + (R_1 L + R_2 L)s + R_1 R_2}{(sR_1 C + 1)(sL + R_2)} \quad (13)$$

The time response of the system described by equation (13) is simulated using the MATLAB® (Mathworks, Natick Mass.) function lsim.

Resistance, capacitance, and inductance values were found by minimizing the error $e_P$ between the desired pressure waveform and the system modeled in (13)

$$e_P = \sqrt{\frac{\sum_{j=1}^{S} |p_j - p_j^m|}{\sum_{j=1}^{S} p_j}} \quad (14)$$

where j is the sample number of S total samples. The MATLAB® function fminsearchbnd was used to achieve this minimization with lower limits of zero for each variable.

Defining $e_p$ in this manner will generate a large error when the desired and modeled pressures are out of phase.

Results

Combining the techniques of Fourier analysis and the inverse Womersley approach, key hemodynamic properties are discovered from in vivo measurements of centerline velocity. Namely, temporal and spatial velocity profiles are found and plotted as well as the temporal volumetric flow and wall shear stress. From this information, the parameters of a blood vessel culture system can be designed to adequately recreate pulsatile and steady physiologic blood-pressure and flow in organ culture using an electro-hydraulic analogy of the 4-element Windkessel model.

The results of a Fourier analysis of the pressure waveforms are shown for a diverse set of 3 blood vessels in Table 1. The various results pertain to the Human Radial Artery (H-RaA), the Human Renal Artery (H-ReA), and the Mouse Aorta (M-AoA).

TABLE 1

Magnitude and phase of blood pressure and flow for each harmonic frequency of the heart rate for the Human Radial Artery (H-RaA), Pig Renal Artery (P-ReA), and Mouse Aorta (M-AoA), as well as the dimensionless Womersley number at each frequency for the vessel.

|  | Heart Rate (Hz) | $M_0^p \ldots M_3^p$ (mmHg) | $\phi_0^p \ldots \phi_3^p$ (rad) | $M_0^q \ldots M_3^q$ (ml/s) | $\phi_0^q \ldots \phi_3^q$ (rad) | $\alpha_0 \ldots \alpha_3$ (..) |
|---|---|---|---|---|---|---|
| H-RaA | — | 94.1 | — | 0.19 | — | — |
| ID = 2.33 mm | 7.87 | 12.8 | 2.81 | 0.05 | 1.75 | 1.64 |
|  | 15.7 | 8.05 | −2.05 | 0.05 | −2.30 | 2.31 |
|  | 23.6 | 4.14 | −0.17 | 0.04 | −1.15 | 2.83 |
| P-ReA | — | 68.3 | — | 1.68 | — | — |
| ID = 3.88 mm | 7.88 | 8.86 | −2.30 | 0.34 | −2.62 | 2.76 |
|  | 15.8 | 6.82 | 0.72 | 0.27 | 0.23 | 3.90 |
|  | 23.7 | 3.56 | −2.99 | 0.178 | −3.08 | 4.78 |
| M-AsA | — | 97.5 | — | 0.21 | — | — |
| ID = 1.20 mm | 65.5 | 16.7 | −2.93 | 0.17 | 1.83 | 2.54 |
|  | 131 | 6.94 | −0.74 | 0.07 | −2.80 | 3.59 |
|  | 196 | 1.36 | 0.91 | 0.04 | −2.59 | 4.39 |

Figure 5A:
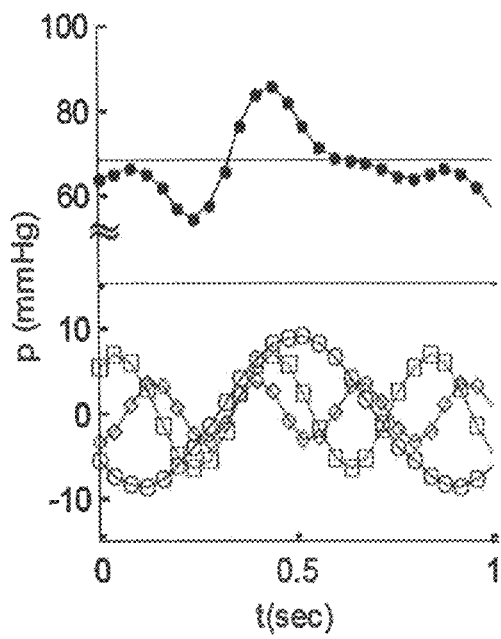
FIG. 5a shows the composite hemodynamic pressure waveform (dotted line) and the mean hemodynamic pressure waveform (n=0; solid line), as well as the fundamental frequency (or first harmonic frequency) component (n=1, open circle waveform), and two harmonic frequency components (n=2, open square waveform and n=3, open diamond waveform) of the composite hemodynamic pressure waveform, from a pig renal artery.
Figure 5B:
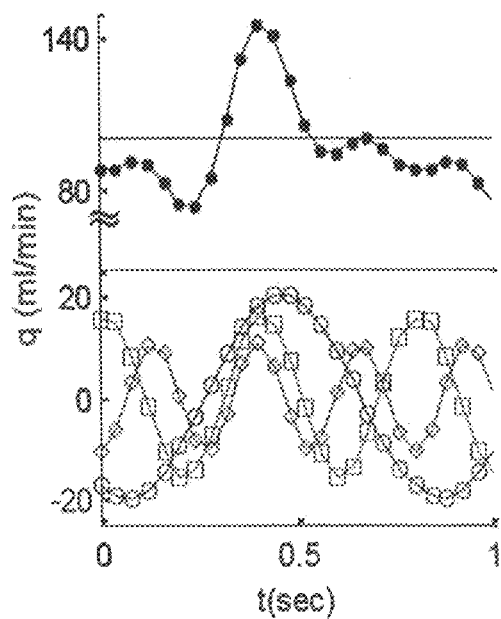
FIG. 5b shows the composite hemodynamic flow waveform (dotted line) and the mean hemodynamic flow waveform (n=0; solid line), as well as the fundamental frequency (or first harmonic frequency) component (n=1, open circle waveform), and two harmonic frequency components (n=2, open square waveform and n=3, open diamond waveform) of the composite hemodynamic flow waveform, from a pig renal artery.

The magnitude and phase of each the fundamental and harmonic frequencies of pressure and flow waveforms are quantified in Table 1 and are shown graphically in FIGS. 5a and 5b for a pig renal artery (P-ReA). The volumetric flow rates shown in Table 1 are calculated using the inverse Womersley method with measured flow velocities and the Fourier Analysis. Specifically, referring to FIGS. 5a and 5b, the composite hemodynamic pressure and flow waveforms from the pig renal artery are shown, where, in FIG. 5a, blood pressure is a measured quantity that is reconstructed using a Fourier analysis, while in FIG. 5b, volumetric flow rate is either provided by Doppler or calculated from the centerline velocity as described. The composite waveforms (dotted lines) in FIG. 5a and FIG. 5b consist of the mean value (n=0, solid line), fundamental frequency component (n=1, open circle waveform), and the n=2 (open square waveform) and n=3 (open diamond waveform) harmonic frequencies shown in FIG. 5a for pressure and in FIG. 5b for volumetric flow. These composite waveforms are similar to the superimposed waveforms shown in FIG. 1. The Reynolds number is a quantity that relates inertial to viscous effects and is given by $$\eta = \frac{2\bar{u} r_i \rho}{\mu} \quad (15)$$

and all calculated Reynolds numbers yield laminar flow results even during peak flow confirming the laminar flow assumption.

Magnitude $M_n$ and phase $\phi_n$ calculations of the mean frequency n=0, the fundamental frequency n=1, and the remaining harmonic frequencies n=2 and n=3 demonstrate the dominance of the low and zero frequency effects on hemodynamics. Of note, a very good representation of blood pressure and flow could be achieved with only the mean, fundamental, and 1 or 2 of the harmonic frequencies. Low Womersley numbers were shown at lower frequencies in the smaller blood vessels that velocity profiles tend towards Poiseuille-type parabolic flow.

Figure 6A:
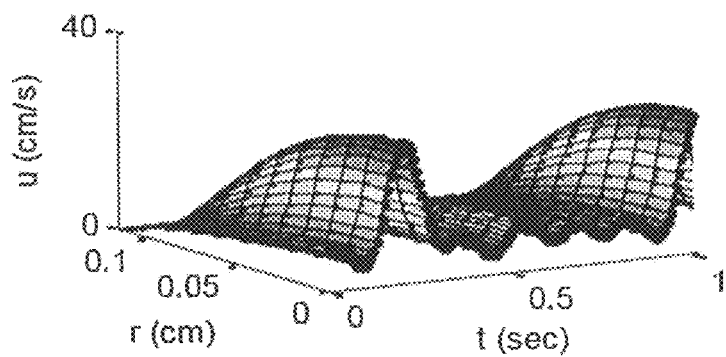
FIGS. 6a-6c show the velocity profiles (3D map) and measured centerline velocity (dotted line) for (a) a Human Radial Artery, (b) a Pig Renal Artery, (c) and a Mouse Aorta.
Figure 6B:
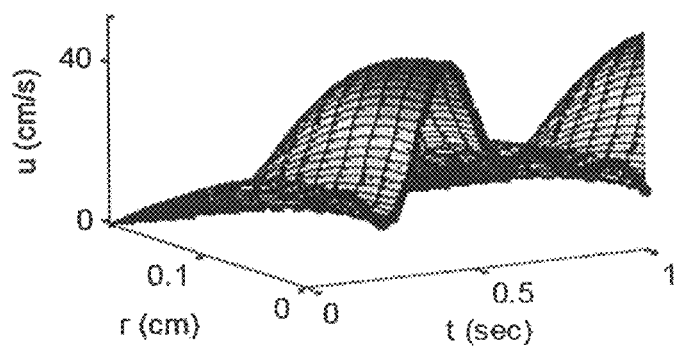
Figure 6C:
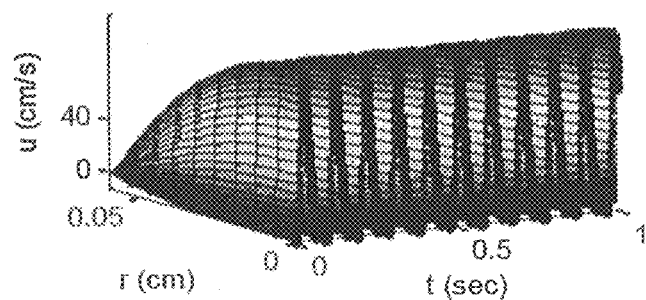

The complete velocity profile across the radius of each blood vessel (a-c) can be seen in FIGS. 6a-6c, where, specifically, FIGS. 6a-6c show the velocity profiles (3D map) and measured centerline velocity (dotted line) for (a) Human Radial Artery, (b) Pig Renal Artery, (c) and Mouse Aorta. For each sample, the centerline velocity is the only measured velocity location based on the digitized literature and superimposed on the figure at r=0. The temporal and spatial differences in velocity profile are apparent.

Figure 7A:
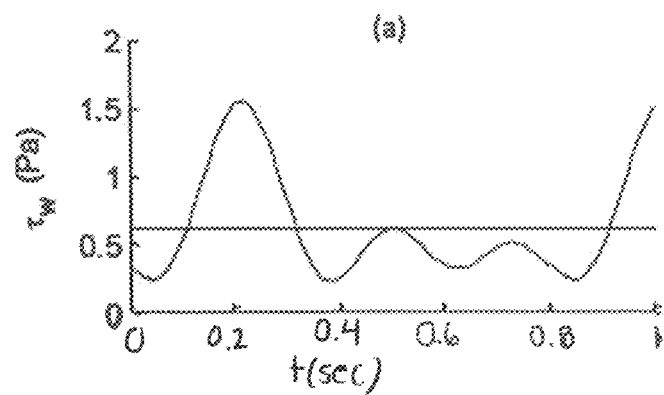
FIGS. 7a-7c show the mean (solid flat line) and pulsatile (solid parabolic/sinusoidal line) wall shear stress ($\tau_w$,) for (a) a Human Radial Artery, (b) a Pig Renal Artery, and (c) a Mouse Aorta.
Figure 7B:
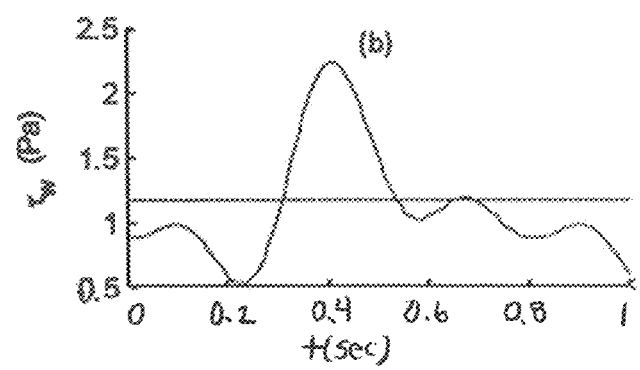
Figure 7C:
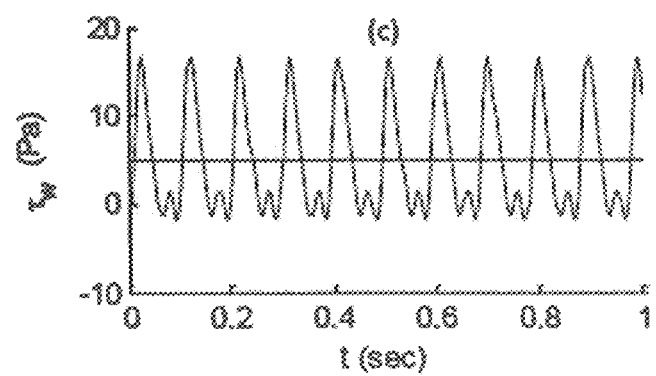

Turning now to FIGS. 7a-7c, using equation (6) the mean (solid flat line) and pulsatile (solid parabolic/sinusoidal line) wall shear stresses ($\tau_w$) are plotted for (a) Human Radial Artery, (b) Pig Renal Artery, (c) and Mouse Aorta for 2 seconds.

Figure 4:
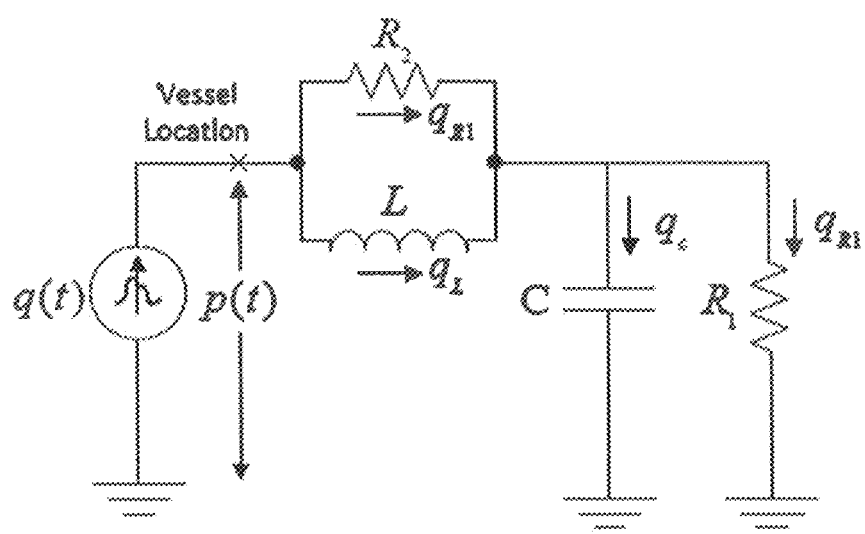
FIG. 4 shows the 4-element Windkessel model as an electro-hydraulic analogy with two resistors, an inductor, and a capacitor, where the location of the blood vessel for culturing is marked with an (x).

The best fit parameters of the 4-element Windkessel simulation, as configured in FIG. 4, are found in Table 2 and are set to minimize the difference between the desired and actual pressure waveforms.

Windkessel model consisting of 2 resistors, a capacitor, and an inductor was used as a basis for hardware design using the electro-hydraulic analogy. The coefficients of the 4-Element Windkessel were found by minimizing the error between the desired and simulated blood pressure waveforms.

As a result of the data collected, the following statements provide a guideline for the construction of the pulsatile perfusion bioreactor of the present invention:

i. The volumetric flowrate q represents the output from a pump or pumps. The current configuration includes a single steady flow pump with constant output equal to that of $M^q_0$ and 3 peristaltic pumps that have a sinusoidal output of magnitude $M^q_{1-3}$ and phase $\phi^q_{1-3}$. Each of the peristaltic pumps would have rotational frequency of $\omega$=n·$\omega$.

ii. The value of resistors $R_1$ and $R_2$ represent the effect of adding a restriction to flow. For $R_1$, the most versatile and biocompatible solution would be to use an electronically controlled pinch valve. $R_2$, on the other hand, must also account for the resistance of the vessel itself so that the total value is $R_2$=(dp/dz)/q+$R_e$ where $R_e$ represents the extra resistance and may take a form similar to that of $R_1$.

iii. The capacitance C is a combination of the compliance of the culture tubing and a compliance chamber. The tubing compliance is dependent upon length, diameter, and material stiffness. The compliance chamber can be assembled with an adjustable volume V of compressible gas so that C=dV/dp and the relationship between the volume and pressure for a gas can be found using the ideal gas law.

iv. The inductance L accounts for the inertia of the blood mass and takes the form L=($\rho$·$\Delta$l)/($\pi r_i^2$). Since the radius of

TABLE 2

Best fit parameters of the 4-element Windkessel model and the cumulative error for each of the mammalian blood vessels described in Table 1

| | $R_1\left(\frac{mmHg \cdot s}{ml}\right)$ | $R_2\left(\frac{mmHg \cdot s}{ml}\right)$ | $C\left(\frac{ml}{mmHg}\right)$ | $L\left(\frac{mmHg \cdot s^2}{ml}\right)$ | $e_p$ |
|---|---|---|---|---|---|
| H-RaA | 503 | 392 | 0.0003 | 4.39 | 0.03 |
| H-ReA | 39.9 | 0.64 | 0.0010 | 10 | 0.10 |
| M-AsA | 485 | 0.56 | 0.0001 | 0.21 | 0.05 |

Figure 8A:
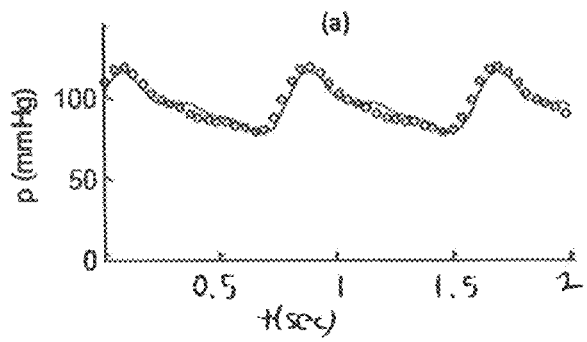
FIGS. 8a-8c show the desired (solid line) and simulated (open circles) pressure responses using the best fit parameters of the electro-hydraulic 4-element Windkessel model. The desired pressure is reported in the literature for (a) a Human Radial Artery, (b) a Pig Renal Artery, (c) and a Mouse Aorta which also shows a zoomed-in section on one mouse cardiac cycle.
Figure 8B:
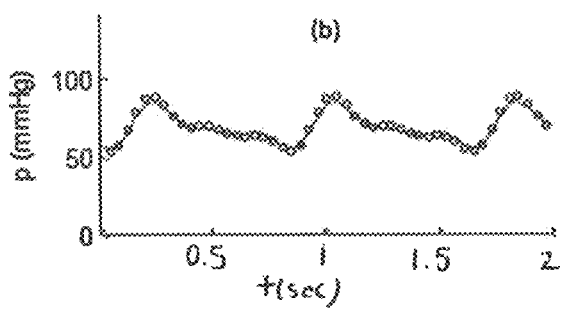
Figure 8C:
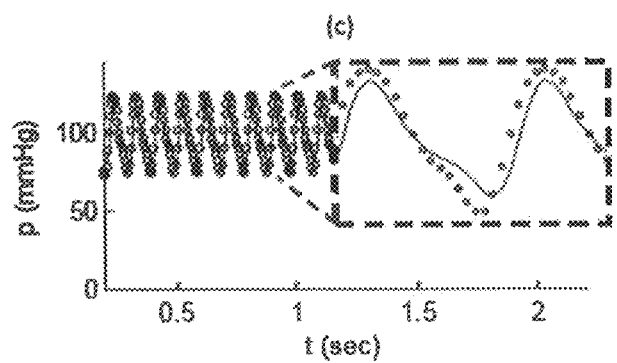

FIGS. 8a-8c demonstrate a plot of desired pressure, based on data obtained from the literature, and the modeling results using the 4-element Windkessel for each blood pressure. Specifically, the desired pressure response is shown as a solid line and the simulated pressure response is shown as open circles pressure responses using the best fit parameters of the electro-hydraulic 4-element Windkessel model. The desired pressure is reported in the literature for (a) Human Radial Artery, (b) Pig Renal Artery, (c) and Mouse Aorta, which also shows a zoomed-in section on one mouse cardiac cycle.

SUMMARY

Hemodynamic studies of the last 45 years have provided a wealth of information that can be used as a baseline to design modern vascular culture systems. In this Example, contemporary blood flow studies were digitized and analyzed using a Fourier transform approach to recreate complex waveforms as mathematical equations consisting of pulsatile pressure and centerline flow velocity. An inverse Womersley approach was used to calculate the velocity profile, volumetric flow, and wall shear stress. A 4-element the vessel remains constant, a shorter or longer section of tissue may be used to adjust this parameter. Additionally, the length l of the vessel may also be limited experimentally so the density of the media can be altered with an additive to match the required value of inductance to compensate.

v. A pressure transducer and flow velocity probe can be used to monitor hemodynamic waveforms. Simple versions, with limited risk for contamination, include a manometer and a vascular Doppler probe.

Example 2

Example 2 demonstrates the ability to culture an EBV in the pulsatile perfusion bioreactor of the present invention over a 10 day culture period where the EBV was subjected to desired stress levels via adjustment of the composite pressure and flow waveforms to which the EBV was exposed, while also maintaining sterility and viability.

Pig tissue was obtained fresh from a local abattoir and dissections were performed immediately following tissue acquisition. Renal arteries were carefully dissected from the surrounding tissue and mounted to our perfusion device using 6.0 braided sutures. All processes occurred while submerged in culture media. The supplemented growth media used in the device consists of Dulbecco's Modified Eagle's Media with 2% heat inactivated fetal bovine serum, 2% L-glutamine, 1000 units/L penicillin, and 1000 g/L streptomycin.

The capacitance was adjusted by changing the volume of air in the compliance chamber. The magnitude and phase angle of each of the channels of the pulsatile pump were adjusted according to Table 2 (ReA). Once the tissue was mounted in the culture chamber, it was placed inside the incubator with the harsh environment camera and connected to the supply and return tubing for both the lumen and reservoir. The LabView program was initiated and the pump motor started under low-pressure, low-flow conditions to remove bubbles. Once bubbles were removed, the pressure control was initiated and culture commenced. A hypertensive culture was also performed for 7 days (not shown) where the magnitude of the steady value of pressure control was 180 mmHg. Every two days for 10 days the culture media was exchanged for fresh media.

At the end of the culture period, vessels were pressurized to 80 mmHg and viability was assessed using Phenylephrine ($10^{-5}$ M) to elicit smooth muscle contraction and carbamocholine chloride to induce nitric oxide dependent vasorelaxation ($10^{-5}$ M). Contractility and dilation were observed for this example. Vessels were removed and prepared for post-culture analysis.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A pulsatile perfusion bioreactor for culturing one or more engineered blood vessels having a lumen and a wall, the pulsatile perfusion bioreactor comprising:
    a chamber for holding the engineered blood vessel and cell culture media;
    a mechanical property monitoring system for measuring and controlling axial tensile stress, circumferential tensile stress, shear stress, or a combination thereof imparted on the wall of the engineered blood vessel and for measuring and controlling axial stretch, circumferential stretch, or a combination thereof imparted on the wall of the engineered blood vessel;
    a pump system for delivering cell culture media through the lumen of the engineered blood vessel, wherein the engineered blood vessel is exposed to a composite pressure waveform and a composite flow waveform as the cell culture media is delivered through the lumen, the pump system comprising a steady flow pump and a peristaltic pump, wherein the composite pressure waveform comprises a mean pressure component, a first harmonic frequency pressure component, and a second harmonic frequency pressure component, and wherein the composite flow waveform component comprises a mean flow component, a first harmonic frequency flow component, and a second harmonic frequency flow component; and
    a computer interface programmed to monitoring and automatically adjust the composite pressure waveform, the composite flow waveform, or a combination thereof in real time to maintain a predetermined axial tensile stress level, a predetermined circumferential stress level, a predetermined shear stress level, or a combination thereof via a feedback loop that integrates mechanical and geometrical information obtained through measurements performed by the mechanical property monitoring system.

2. The bioreactor as in claim 1, wherein the composite pressure waveform and the composite flow waveform are derived from a pressure waveform and a flow waveform of a native blood vessel, wherein the engineered blood vessel is a replacement for the native blood vessel.

3. The bioreactor as in claim 1, wherein the steady flow pump delivers the mean pressure component of the composite pressure waveform and the mean flow component of the composite flow waveform.

4. The bioreactor as in claim 1, wherein the peristaltic pump delivers a pulsatile flow of cell culture media through the lumen, wherein the peristaltic pump comprises a first pump head and a second pump head, wherein the first pump head provides the first harmonic frequency pressure component of the composite pressure waveform and the first harmonic frequency flow component of the composite flow waveform, and wherein the second pump head provides the second harmonic frequency pressure component of the composite pressure waveform and the second harmonic frequency flow component of the composite flow waveform.

5. The bioreactor as in claim 4, wherein the peristaltic pump further comprises a third pump head, wherein the third pump head provides a third harmonic frequency pressure component of the composite pressure waveform and a third harmonic frequency flow component of the composite flow waveform.

6. The bioreactor as in claim 1, further comprising a compliance chamber.

7. The bioreactor as in claim 1, further comprising a pressure transducer.

8. The bioreactor as in claim 1, further comprising a stepper motor controlled pinch valve.

9. The bioreactor as in claim 1, further comprising a camera for measuring the engineered blood vessel length, wall diameter, and wall thickness.

10. The bioreactor as in claim 1, wherein the chamber is located in an incubator.

11. The bioreactor as in claim 1, wherein the engineered blood vessel comprises a natural material or a synthetic material.

12. The bioreactor as in claim 1, wherein the engineered blood vessel includes endothelial cells.

13. The bioreactor as in claim 1, wherein the engineered blood vessel includes smooth muscle cells.

* * * * *